United States Patent
Lu

(10) Patent No.: US 6,952,612 B1
(45) Date of Patent: Oct. 4, 2005

(54) METHOD AND APPARATUS FOR PROGRAMMING A RATE RESPONSIVE IMPLANTABLE CARDIAC STIMULATION DEVICE USING USER SPECIFIED RATE RESPONSE FUNCTIONS

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 614 days.

(21) Appl. No.: 10/132,445

(22) Filed: Apr. 24, 2002

(51) Int. Cl.[7] ............................................. A61N 1/372
(52) U.S. Cl. ........................................ 607/30; 607/17
(58) Field of Search .............................. 607/17, 18, 27, 607/30, 31, 59

(56) References Cited

U.S. PATENT DOCUMENTS

| | | | |
|---|---|---|---|
| 4,399,820 A | 8/1983 | Wirtzfield et al. | 128/419 PG |
| 4,644,954 A | 2/1987 | Wittkampf et al. | 128/419 PG |
| 4,759,366 A | 7/1988 | Callaghan | 128/419 PG |
| 4,865,036 A | 9/1989 | Chirife | 128/419 PG |
| 5,097,831 A | 3/1992 | Lekholm | 128/419 PG |
| 5,101,824 A | 4/1992 | Lekholm | 128/419 PG |
| 5,154,171 A | 10/1992 | Chirife | 128/419 PG |
| 5,271,395 A | 12/1993 | Wahlstrand et al. | 607/9 |
| 5,431,691 A | 7/1995 | Snell et al. | 607/27 |
| 5,466,254 A | 11/1995 | Helland | 607/123 |
| 5,716,382 A | 2/1998 | Snell | 607/30 |
| 5,800,473 A * | 9/1998 | Faisandier | 607/59 |
| 5,824,020 A | 10/1998 | Cooper | 607/17 |
| 5,913,879 A | 6/1999 | Ferek-Petric et al. | 607/14 |
| 5,944,743 A | 8/1999 | Janssens | 607/9 |
| 5,957,957 A | 9/1999 | Sheldon | 607/17 |
| 5,974,341 A | 10/1999 | Er et al. | 607/31 |
| 6,058,326 A | 5/2000 | Hess et al. | 607/9 |
| 6,058,328 A | 5/2000 | Levine et al. | 607/14 |
| 6,128,534 A | 10/2000 | Park et al. | 607/17 |
| 6,129,744 A | 10/2000 | Boute | 607/25 |

\* cited by examiner

*Primary Examiner*—George R. Evanisko

(57) ABSTRACT

Techniques are provided for programming a rate-responsive pacemaker or other implantable cardiac stimulation device capable of rate-responsive pacing. In one embodiment, an external programmer is configured to allow a physician to program the pacemaker with a smooth curvilinear rate-responsive pacing function having whatever shape the physician deems optimal for the patient, rather than being limited to generating a linear or bi-linear rate-responsive pacing functions as with many conventional techniques. The rate-responsive pacing function may specify, for example, pacing rates as a function of orthostatic sensor values, activity sensor values, minute ventilation sensor values, vasovagal syncope sensor values or paced depolarization integral sensor values. If several sensors are provided in the pacemaker, smooth rate-responsive pacing functions may be separately generated for use with each sensor.

18 Claims, 8 Drawing Sheets

METHOD AND APPARATUS FOR PROGRAMMING A RATE RESPONSIVE IMPLANTABLE CARDIAC STIMULATION DEVICE USING USER SPECIFIED RATE RESPONSE FUNCTIONS

CROSS-REFERENCE TO RELATED APPLICATIONS

This application is related to copending U.S. patent application Ser. No. 10/132,770, titled "Method and Apparatus for Programming a Rate Responsive Implantable Cardiac Stimulation Device Using User Specified Rate Response Functions," filed concurrently herewith.

FIELD OF THE INVENTION

The invention generally relates to implantable cardiac stimulation devices and to external programmer devices for use in connection therewith.

BACKGROUND OF THE INVENTION

Implantable cardiac stimulation devices, such as pacemakers, are often configured to be used in conjunction with an external programmer that allows a physician to program the operation of the implanted device to, for example, control the specific parameters by which the implanted device detects a heart arrhythmia and responds thereto. For instance, the programmer may allow the physician to specify the sensitivity with which the cardiac stimulation device senses electrical signals within the heart and to further specify the amount of electrical energy to be employed for pacing the heart in circumstances where expected heart signals are not sensed. If the cardiac stimulation device includes a physiological sensor, the programmer may also permit the physician control in the manner by which the device responds to signals generated by the sensor. Examples of sensors include minute ventilation sensors for detecting respiration signals, temperature sensors, oxygen blood saturation sensors and the like.

In many cases, a sensor is used for rate-responsive pacing whereby the cardiac stimulation device determines the rate at which the heart of the patient is to be paced based on the conditions detected by the sensor. In one specific example, the pacing rate is determined based on the impedance signal measured by a minute ventilation sensor. FIG. 1 illustrates a minute ventilation response graph displayed by an external programmer, which relates minute ventilation values to pacing rates. In use, the external programmer generates a bi-linear minute ventilation response graph 10 for display to the physician based on an initial set of control parameters. The physician can modify the set of control parameters and display the resulting adjusted bi-linear response function 20. The physician then selects either the initial set or the modified set of control parameters, which are transmitted to the implantable device for use therein. Thereafter, the stimulation device uses the selected control parameters to automatically calculate a pacing rate based on the calculated minute ventilation signals as detected by the sensor, then the device paces the heart at the calculated sensor indicated rate. Assuming the rate-response control parameters have been properly selected, the stimulation device can approximate a healthy sinus node response by increasing the pacing rate as the level of physical exertion of the patient increases as detected by increased ventilation in the lungs.

Although rate-responsive pacing has proven to be effective for mimicking the response of a healthy sinus node, room for improvement remains. In the conventional system summarized above, the rate-response control parameters that the physician can select only define bi-linear rate-response functions, i.e. the resulting rate response graphs of FIG. 1 are defined by two straight segments. It appears, however, the actual relationship of minute ventilation to sinus rate is curvilinear in most patients. As such, a physician using a programming system limited to bi-linear rate-responsive pacing functions may not be able to program the device to mimic the response of a healthy sinus node as closely as might be preferred. Accordingly, it would be highly desirable to provide an improved technique for programming implantable cardiac stimulation devices, which permits more flexible programming of rate-responsive pacing functions, such as minute ventilation functions, and it is to this end that aspects of the invention are directed.

If two or more sensors are used, the implantable cardiac stimulation device typically combines the pacing rates determined from the separate sensors to yield a single pacing rate. For example, if the device includes both a minute ventilation sensor and an activity sensor, the device may determine one pacing rate based on the minute ventilation and another rate based on the activity level then combine the rates to yield a final pacing rate for use in pacing the heart. Typically, the microcontroller of the cardiac stimulation device is programmed to combine the pacing rates from the sensors in a fixed predetermined manner regardless of the current level of exertion of the patient. For example, the microcontroller may be programmed to average the two pacing rates to yield the final pacing rate. Hence, the two sensors contribute equally to the determination of the final pacing rate regardless of the current level of exertion. However, one sensor may be more effective than another at different levels of exertion. It would be preferable, therefore, to permit the physician to select the relative contributions of multiple sensors for different levels of exertion and it is to this end that other aspects of the invention are directed.

Also, many conventional implantable cardiac stimulation devices permit programming of only a single rate-responsive pacing function for each sensor. In some cases, however, it would be preferable to permit programming of different rate-responsive pacing functions depending upon the general condition of the patient. For example, if the patient is in a prolonged state of bed rest, then a rate-response function programmed with the expectation that the patient will be more active may be too aggressive resulting in unnecessarily high heart rates. In contrast, if the patient is generally active, then a rate-response function programmed with the expectation that the patient will be primarily at bed rest may be too passive resulting in generally lower heart rates than optimal. Accordingly, it would be preferable to permit the programming of several rate-responsive pacing functions for each sensor for use under different conditions and it is to that end that still other aspects of the invention are directed.

SUMMARY

In accordance with a first aspect of the invention, a technique is provided for programming an implantable cardiac stimulation device with a rate-responsive pacing function having a user selected curvilinear shape. The user inputs a set of individual values (e.g. numerically or graphically) representative of points defining a desired rate-responsive pacing function into an external programmer, which fits a curvilinear function to the input values to generate a smooth rate-responsive pacing function. The smooth rate-responsive pacing function is then converted to a look-up table of pacing rates as a function of sensor values by the implantable device or the table is transmitted from the programmer to the implantable device for use therein. In this manner, a physician may program the implanted device with a rate-responsive pacing function having whatever shape the physician deems optimal, rather than being limited to merely selecting control parameters that correspond to linear or bi-linear functions as in many conventional rate responsive pacing programming techniques. Depending upon the implantable cardiac stimulation device, the smooth rate-responsive pacing function generated by the external programmer may specify, for example, pacing rates as a function of orthostatic sensor values, activity sensor values, minute ventilation sensor values, vasovagal syncope sensor values or paced depolarization integral sensor values. If several sensors are provided in the implantable device, smooth rate-responsive pacing functions may be sparely generated for use with each sensor.

In accordance with a second aspect of the invention, a technique is provided for programming an implantable cardiac stimulation device to combine the contributions from several sensors using user selected relative contribution percentages. Specific percentage sensor contributions are input from a user by an external programmer, and then transmitted to the cardiac stimulation device for use in calculating a pacing rate. In this manner, a physician using the external programmer may program the implanted device to combine the contributions from several sensors using whatever contributions the physician deems optimal, rather than being limited to fixed percentage contributions as required with many conventional rate-responsive pacing programming techniques. The combined rate responsive functions can also be converted to a look-up table of pacing rates as a function of combined sensor values by the implantable device or the table is transmitted to the device from the programmer for use therein. Moreover, the physician can specify different percentage contributions to be employed for different levels of exertion of the patient. In one example, the percentage of contribution of an activity sensor is 100% at the onset of exercise; the percentage of contribution of a paced depolarization interval sensor is 100% at maximum exertion; and percentage contributions of the two sensors are weighted there between.

In accordance with a third aspect of the invention, a technique is provided for programming an implantable cardiac stimulation device with different rate-responsive pacing functions for use under different conditions, such as different general activity levels of the patient. A set of individual rate-responsive pacing functions is generated using an external programmer, each having differing response characteristics. Numerical representations of the rate-responsive pacing functions are transmitted to the cardiac stimulation device for use therein. Then, criteria specifying the circumstances under which each of the selected rate-responsive pacing functions are to be employed are input by the external programmer and transmitted to the cardiac stimulation device for use therein. In this manner, a physician using the external programmer may program the implanted cardiac stimulation device to use different rate-responsive pacing functions depending upon the current condition of the patient, rather than being limited to using a single rate-responsive pacing function as required by many conventional implantable devices. Different rate-responsive pacing functions may be used, for example, depending upon whether the patient is at bed rest or is active or depending upon whether the patient is having frequent tachyarrhythmia episodes.

Also, in accordance with the invention, external programmers and implantable cardiac stimulation devices may be configured to exploit various combinations of the aforementioned features of the invention. For example, an external programmer can be provided which not only permits a physician to generate multiple smooth rate response functions for each sensor but also allows the physician to specify the percent contributions of the sensors.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 2:
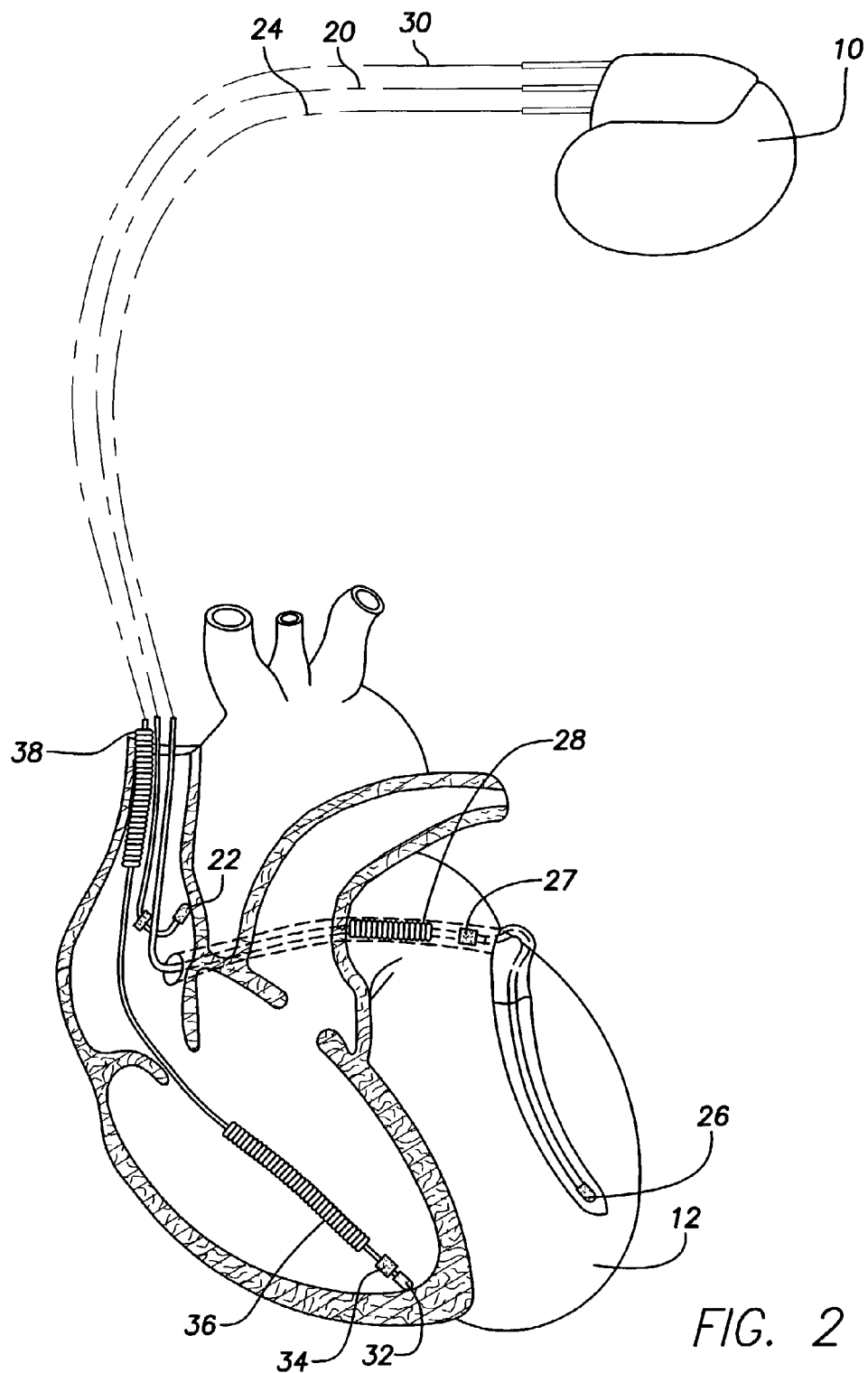
FIG. 2 is a simplified diagram illustrating an implantable stimulation device in electrical communication with at least three leads implanted into a patient's heart for delivering multi-chamber stimulation and shock therapy.

As shown in FIG. 2, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 3:
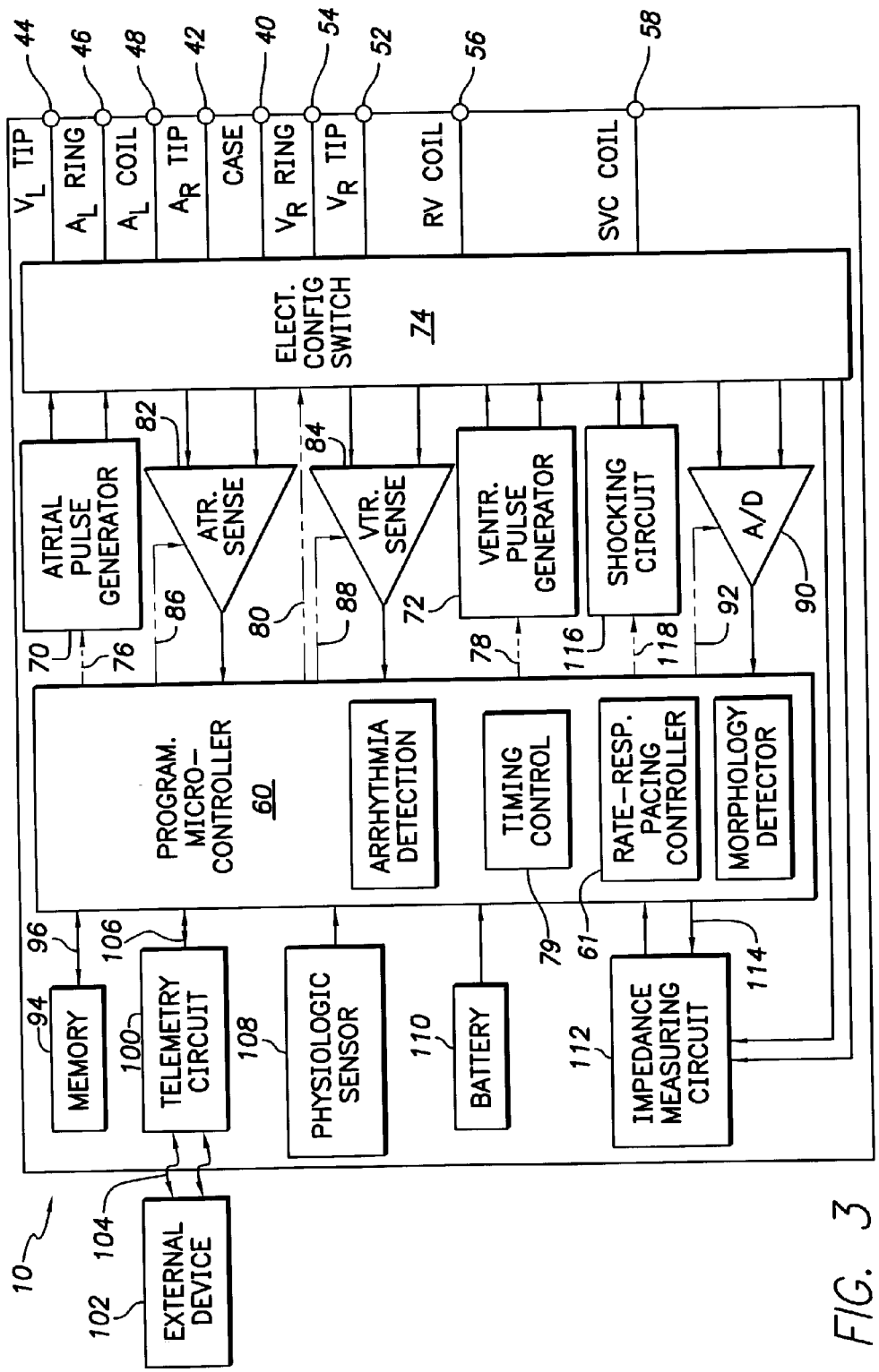
FIG. 3 is a functional block diagram of a multi-chamber implantable stimulation device illustrating the basic elements of a stimulation device, which can provide cardioversion, defibrillation and pacing stimulation in four chambers of the heart, and having an improved rate-responsive pacing controller configured in accordance with the invention.

As illustrated in FIG. 3, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Microcontroller 60 controls the operation of the stimulation device using various control parameters received from the external programmer.

As shown in FIG. 3, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device additionally includes a battery 110 that provides operating power to all of the circuits shown in FIG. 3. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 3, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Stimulation device 10 further includes one or more sensors 108, commonly referred to as "rate-responsive" sensors because they are typically used to adjust pacing stimulation rate according to the exercise state of the patient. However, sensor 108 may further be used to detect changes in cardiac output, changes in the physiological condition of the heart, or diurnal changes in activity (e.g., detecting sleep and wake states). Microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that sensors 108 may also be external to the stimulation device 10, yet still be implanted within or carried by the patient.

Examples of sensors include: minute ventilation sensors (also known as minute volume sensors) for detecting the total volume of air moved in and out of the lungs in one minute; orthostatic sensors for detecting the physical inclination of the patient; activity variance sensors for detecting a degree of physical activity of the patient; vasovagal syncope sensors for detecting whether the patient is prone to an episode of vasovagal syncope; paced depolarization integral (PDI) sensors (also known as ventricular gradient sensors) for calculating the integral of a paced R-wave; QT interval sensors for detecting the time between ventricular polarization (Q-wave) and ventricular re-polarization (T-wave); temperature sensors; oxygen blood saturation sensors; and pre-ejection period (PEP) sensors for detecting the time interval between the onset of ventricular activation (i.e. the onset of a QRS complex) and the onset of ventricular ejection (i.e. the opening of the aortic and pulmonic valves).

For a description of a minute ventilation sensors, see U.S. Pat. No. 5,824,020 to Cooper. For a description of an orthostatic sensor, see U.S. Pat. No. 5,957,957 to Sheldon. For a description of an activity variance sensor, see U.S. Pat. No. 6,128,534 to Park et al. For a description of a vasovagal syncope sensor, see U.S. Pat. No 5,913,879 to Ferek-Petric, et al. For a description of PDI, also known as the ventricular depolarization gradient, see U.S. Pat. No. 4,759,366, to Callaghan. For a description of QT interval, also known as the stimulus-to-evoked T-wave, see U.S. Pat. No. 4,644,954, to Wittkampf et al. For a description of oxygen saturation, see U.S. Pat. No. 4,399,820, to Wirtzfeld et al. For descriptions of pre-ejection period and ejection fraction sensors, see U.S. Pat. Nos. 4,865,036 and 5,154,171, both to Chirife. Each of the aforementioned patents is incorporated herein by reference.

Microcontroller 60 includes a rate-responsive pacing controller 61, which processes signals from one or more sensors and determines a pacing rate based on the sensor values. The manner by which a physician programs the stimulation device to perform rate-responsive pacing and the manner by which the rate-responsive pacing controller processes signals received from the sensors will be described in detail below with reference to FIGS. 5–10.

Overview of External Programmer

Figure 4:
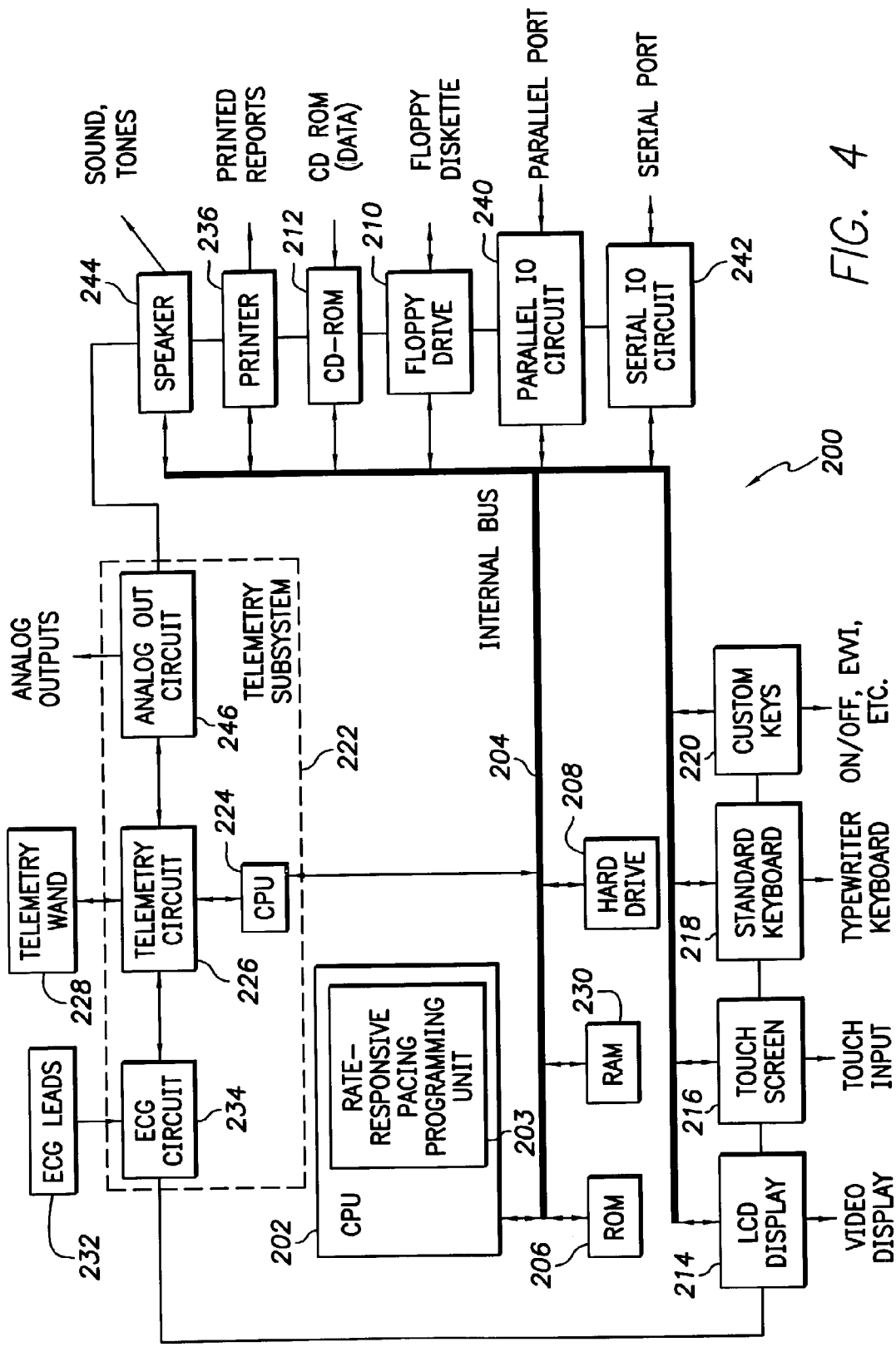
FIG. 4 is a functional block diagram illustrating components of a programmer for use in programming the implantable device of FIG. 2, and having an improved rate-responsive pacing programming unit.

FIG. 4 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an EVVI key.

Typically, the physician initially controls the programmer 200 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via the internal bus. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Preferably, all data stored within the implanted device is recorded within "event records" which facilitate the efficient storage and transmission of the data. Additional information pertaining to the recording, transmission, and processing of event record information may be found within U.S. Pat. No. 5,431,691 to Snell et al. entitled "Method and System for Recording and Displaying a Sequential Series of Pacing Events". Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device.

The CPU includes a rate-responsive pacing programming unit 203 for use in programming sensor response functions for use with the various sensors of the implantable device. As will be explained below the rate-responsive pacing programming unit coordinates the generation of smooth user-selected sensor response functions, the programming of user-selected percentage contributions for different sensors, and the programming of separate sensor response functions for use under different patient conditions.

Techniques for programming an implanted medical device may be found in U.S. Pat. No. 5,716,382 entitled "Programmer For An Implantable Cardiac Stimulating Device". Prior to reprogramming specific parameters, the physician may control the external programmer to display any or all of the data retrieved from the implanted device or from the ECG leads, including displays of ECGs, IEGMs, and statistical patient information. Further information pertaining to the types of information which may be displayed using programmer may be found in U.S. Pat. No. 5,974,341 entitled "Method And Apparatus For Detecting And Displaying Diagnostic Information In Conjunction With Intracardiac Electrograms And Surface Electrocardiograms". Any or all of the information displayed by programmer may also be printed using a printer 236.

Programmer 200 also includes a serial port 240 and a parallel port 242 for connecting to other device, not shown, such as modems and the like. Although one of each is shown, a plurality of input output (IO) ports might be provided.

A speaker 244 is included for providing audible tones to the user, such as a warning beep in the event the physician provides improper input. Telemetry subsystem 222 additionally includes an analog output circuit 246 for controlling the transmission of analog output signals.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 4 are intended merely to provide an overview of the operation of programmer and are not intended to describe in detail each and every feature of the hardware and software of the device and is not intended to provide an exhaustive list of the functions performed by the device.

Physician-Specified Rate-Responsive Pacing Functions

Figure 5:
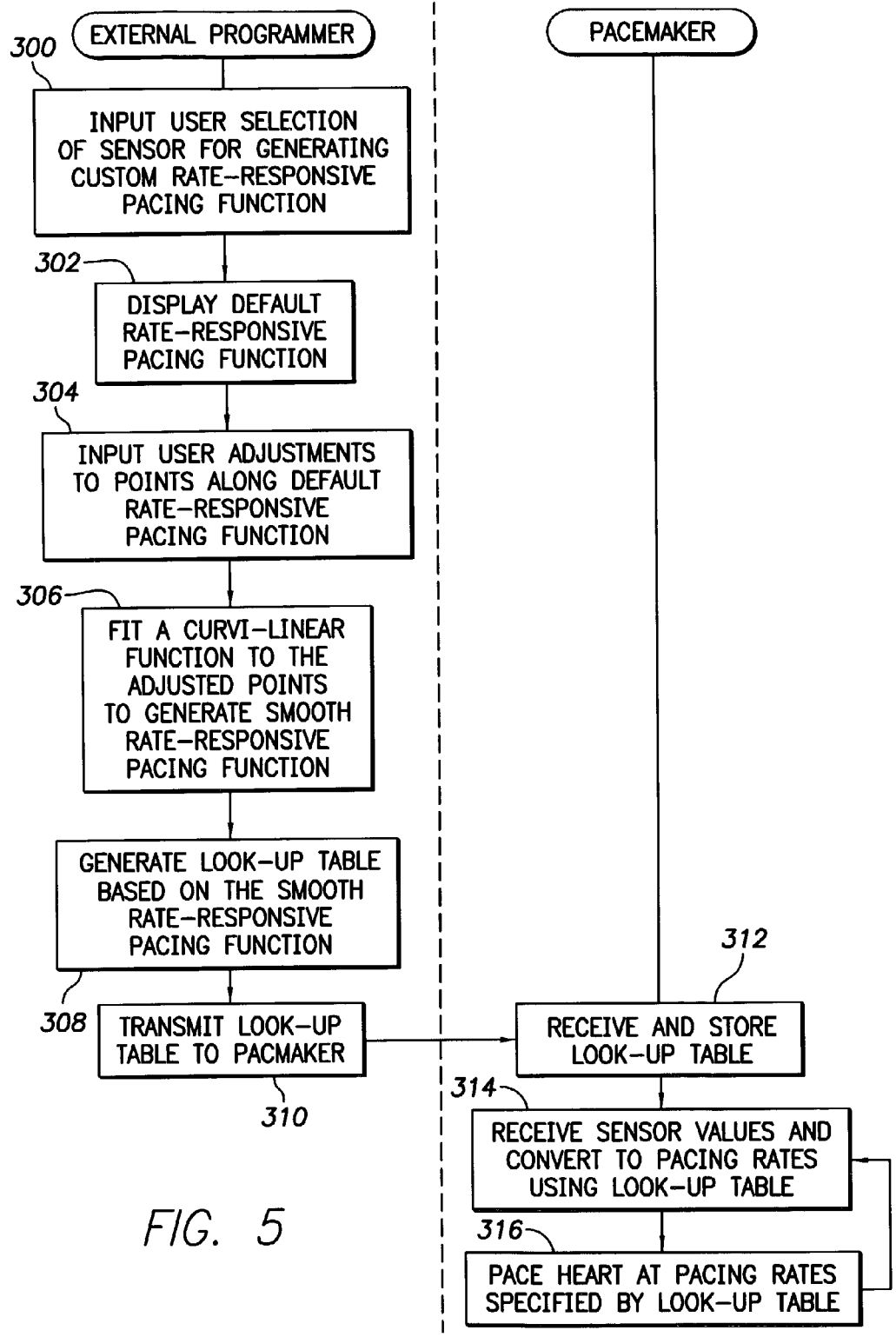
FIG. 5 is a flow chart illustrating an exemplary method for programming the implanted device of FIGS. 2 and 3 using the external programmer of FIG. 4 wherein the implanted device is programmed with smooth rate-response functions.
Figure 6:
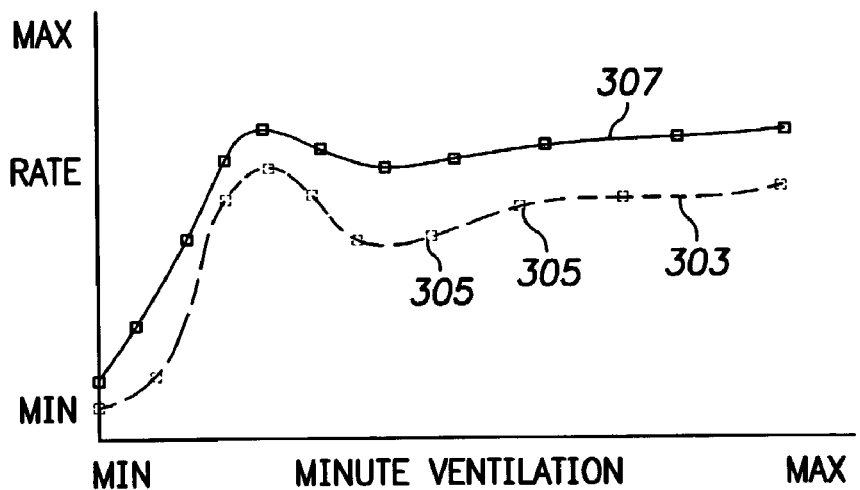
FIG. 6 is a graph illustrating exemplary smooth rate-response functions programmed using the method of FIG. 5.

The flow chart of FIG. 5 illustrates the generation of smooth user-specified rate-responsive pacing functions for use in programming a cardiac stimulation device implanted within a patient. In the flow chart of FIG. 5, and in other flow charts provided herein, various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein. In the flow charts, operations performed by the external programmer of FIG. 4 are shown on the right and operations performed by the pacemaker of FIG. 3 are shown on the left.

Initially, at step 300, rate-responsive pacing programming unit 203 of the external programmer (FIG. 4) displays a list of the sensors available within the implanted device and the physician, or other specialist operating the external programmer, selects one of the sensors for programming. The implantable device may have, for example, one or more of a minute ventilation sensor; an orthostatic sensor; an activity variance sensor; a vasovagal syncope sensor; a PDI sensor; a QT interval sensor; a temperature sensor; an oxygen blood saturation sensor; and a PEP sensor. At step 302, the programmer displays a default smooth rate-responsive pacing function for the selected sensor. The default rate-responsive pacing function relates sensor values to pacing rates, such as minute ventilation values to pacing rates. An exemplary default function 303 displayed by the external programmer for use with a minute ventilation sensor is shown in phantom lines in FIG. 6. The horizontal or x-axis of the graph represents the amount of minute ventilation in arbitrary units from a minimum amount to a maximum amount. The vertical or y-axis of the graph represents the rate at which the heart is to be paced in arbitrary units from a minimum rate, such as 55 beats per minute (bpm), to a maximum amount, such as 140 beats per minute (bpm). The default rate-responsive pacing function is represented by a set of discrete points 305 connected by straight lines. The number of points used to represent the default rate-responsive pacing function may be preprogrammed or may be selected by the physician.

At step 304, the physician adjusts the shape of the default rate-responsive pacing function to generate a new sensor response function 307 of arbitrary shape. Adjustment is achieved by an appropriate input technique, such as by using a mouse-pointing device to select and drag individual points 305 within the graph of FIG. 6 to new positions. At step 306, the external programmer fits a smooth spline function to the adjusted points and displays the resulting smooth function 309. In this manner, the physician may define a rate-response curve having any shape so as to best address the requirements of the particular patient. At step 308, the programmer generates a look-up table based on the smooth function. The look-up table provides a pacing rate for each corresponding sensor value for, for example, one hundred or one thousand incremental values throughout a range of acceptable sensor values. In other words, for each of a thousand incremental minute ventilation values from a minimum minute ventilation values to a maximum value, the look up table stores a single pacing rate. The look-up table is transmitted to the implanted device at step 310 and stored therein at step 312. Beginning at step 314 the rate-responsive pacing controller of the implanted device (unit 61 of FIG. 4) receives output values from the selected sensor and determines pacing rates using the values of the look-up table. For a minute ventilation sensor, for example, if the minute ventilation is found to be near a maximum, the look-up table might specify a pacing rate of 120 beats per minute (bpm) whereas if the minute ventilation is found to be near a minimum, the look-up table might specify a pacing rate of only 60 bpm. At step 316, the implanted device then paces the heart at the determined pacing rate. Alternative programming techniques may instead be used instead of look-up tables. For example, the spline parameters generated in connection with fitting the spline curve to the selected points may be transmitted to the implanted device, which converts sensor values to pacing rates by performing numerical computations using the spline parameters.

If multiple sensors are provided, steps 300–310 are repeated to generate rate-responsive pacing look-up tables for each selected sensor, and the separate look-up tables are transmitted to and stored in the implanted device. As will be explained with reference to FIGS. 7 and 8, the physician may program the relative percentage contributions of the multiple sensors to determining the pacing rate. Also, as will be explained with reference to FIGS. 9 and 10, the physician may program multiple rate-responsive pacing functions for each individual sensor for use under different patient conditions.

Physician-Specified Sensor Contributions

Figure 7:
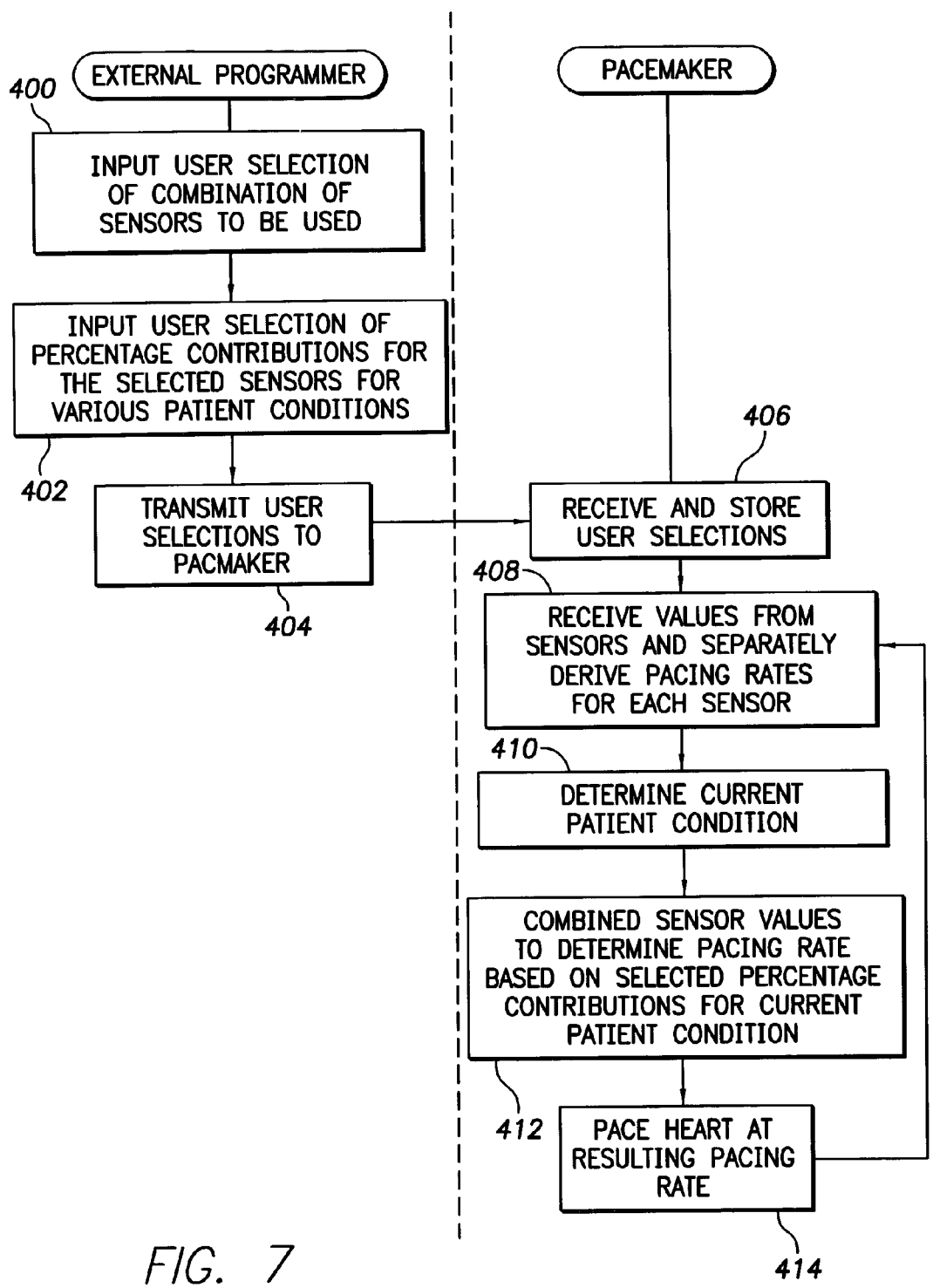
FIG. 7 is a flow chart illustrating an exemplary method for programming the implanted device of FIGS. 2 and 3 using the external programmer of FIG. 4 wherein the implanted device is programmed with sensor contribution percentages as a function of patient exertion level.

The flow chart of FIG. 7 illustrates the programming of user-specified percentage contributions for use in combining values from multiple sensors within a cardiac stimulation device implanted within a patient. At step 400, rate-responsive pacing programming unit 203 of the external programmer (FIG. 4) displays a list of the sensors and the physician selects a combination of two or more of the sensors. The implantable device may have combinations of two or more of a minute ventilation sensor; an orthostatic sensor; an activity variance sensor; a vasovagal syncope sensor; a PDI sensor; a QT interval sensor; a temperature sensor; an oxygen blood saturation sensor; and a PEP sensor. At step 402, the programmer displays a default sensor percentage contribution function for the selected sensors for various exercise levels or other patient conditions. The exercise levels may be, for example, "rest", "onset of exertion", and "maximum exertion" or perhaps "below anaerobic threshold" and "above anaerobic threshold".

Figure 8:
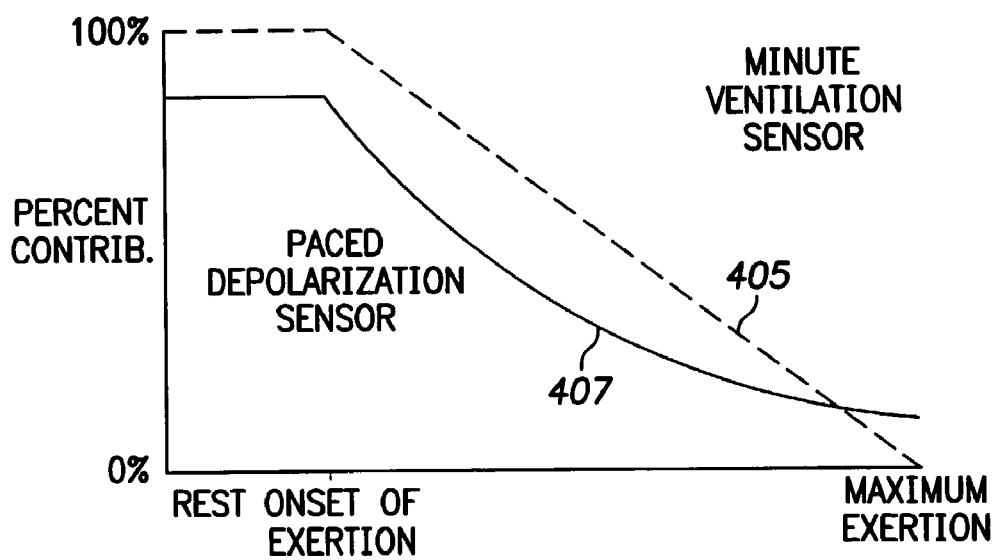
FIG. 8 is a graph illustrating exemplary percentage contributions as a function of patient exertion level programmed using the method of FIG. 7.

An exemplary graph 405 representing default percentage contributions as a function of level of exertion for a combination of a minute ventilation sensor and a paced depolarization sensor is shown in phantom lines in FIG. 8. The horizontal or x-axis of the graph represents the level of exertion in arbitrary units from rest through minimum exertion to maximum exertion. The level of exertion may be quantified, for example, by intrinsic heart rate, paced rates, minute ventilation rates, etc. The vertical or y-axis of the graph represents the percentage contribution of the two sensors with the default percent contribution of the paced depolarization sensor being represented by the values below the phantom line and the default percent contribution of the minute ventilation sensor being represented by the values above the phantom line. As can be seen, while the patient is at rest the percentage contribution of the paced depolarization sensor is 100%. Beginning with the onset of exertion, however, the percentage contribution of the paced depolarization sensor begins to decrease and the percentage contribution of the minute ventilation sensor begins to increase until, at maximum exertion, the percentage contribution of the minute ventilation sensor is 100%. At exertion levels between the onset of exertion and maximum exertion, the relative contribution percentages of the two sensors vary linearly. Alternatively, rather than providing a sensor percent contribution function that provides potentially different percent contribution values for each incremental level of exertion throughout a range of exertion levels, individual sets of percent contribution values may be specified for each general level of exertion. In other words, one set of percent contribution values are specified for "rest", another for "minimal exertion", and yet another for "maximum exertion. As can be appreciated, a wide range of specific techniques may be provided consistent with the invention.

Continuing with FIG. 7, at step 402, the programmer inputs user adjustments, if any, to the default sensor percentage contribution function. Adjustments may be input, for example, by displaying individual points along the function and permitting the points to be manually adjusted as with the technique above. Once the individual points along the sensor contribution function have been adjusted, the external programmer either fits straight lines between the points or fits a spline to generate a curved sensor contribution function. An exemplary curved sensor contribution function 407 representing adjusted percentage contributions as a function of level of exertion is also shown in FIG. 8. As can be seen, while the patient is at rest, the percentage contribution of the paced depolarization sensor is about 80%. Beginning with the onset of exertion, the percentage contribution of the paced depolarization sensor decreases until, at maximum exertion, the percentage contribution of the paced depolarization sensor is about 15%. At exertion levels between the onset of exertion and maximum exertion, the relative contribution percentages of the two sensors vary non-linearly as shown.

The resulting sensor percentage contribution function is transmitted to the implanted device at step 404 for storage therein at step 406. To this end, the sensor percentage contribution function can be converted to a look-up table. Other programming techniques may instead be used. In any case, beginning at step 408, the rate-responsive pacing controller of the implanted device (unit 61 of FIG. 4) receives values from the sensors of the device and separately computes pacing rates for each selected sensor using look-up tables of the type described above in connection with FIG. 5 or using any other suitable technique. At step 410, the rate-responsive pacing controller then determines the current condition or status of patient, such as the current exercise level of the patient, i.e. at rest, at the onset of exertion, or at maximum exertion. The patient condition may be determined, for example, based on values received from one of the selected sensors, such as from the minute ventilation sensor, or based on previously determined pacing rates. For example, if the sensor contribution graph of FIG. 8 is represented as a function of minute ventilation values, then the current values output from the minute ventilation sensor are used to determine the current level of exertion of the patient at step 410. If the sensor contribution graph of FIG. 8 is represented as a function of pacing rates, then the most recently determined pacing rate is used to determine the current level of exertion of the patient at step 410.

At step 412, the rate-responsive pacing controller combines the pacing rates derived at step 408 using the contribution percentages specified by the percent contribution function for the patient condition determined at step 410 to generate a resulting weighted pacing rate at which the heart is paced at step 414. To this end, the rate-responsive pacing controller first determines the percent contributions of the sensors based on the current patient condition (e.g. the current level of exertion) using the percent contribution function (FIG. 8). Then, the rate-responsive pacing controller combines the pacing rates derived at step 408 to yield a new pacing rate. Consider an example wherein the individual pacing rates derived from the minute ventilation sensor and the paced depolarization sensor are 85 bpm and 78 bpm, respectively. If minute ventilation indicates that the patient is at rest, then the rate-responsive pacing controller first determines the respective contributions of the minute ventilation sensor and the paced depolarization sensor while the patient is at rest are, for example, 80% and 20%. Then, the rate-responsive pacing controller combines the respective individual pacing rates derived from the sensors (85 bpm and 78 bpm) using the percentage contributions of 80% and 20% (by calculating 0.8*85+0.2* 78) to yield an 83.6 bpm. Hence, the heart is paced at a rate of 83.6 bpm.

Physician-Specified Condition-Dependent Pacing Functions

Figure 1:
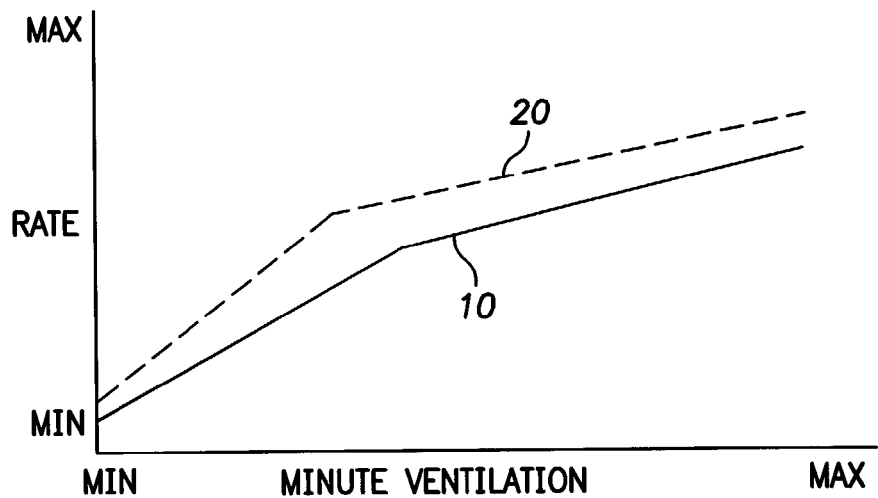
FIG. 1 is a graph illustrating bi-linear rate-response functions displayed by an external programmer configured in accordance with the prior art.
Figure 10:
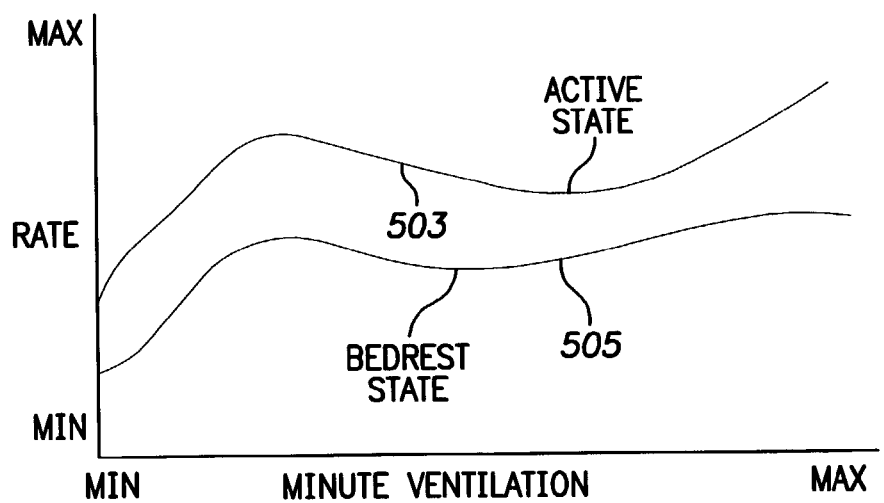
FIG. 10 is a graph illustrating a set of exemplary rate-response functions for use under different patient conditions as programmed using the method of FIG. 9.
Figure 9:
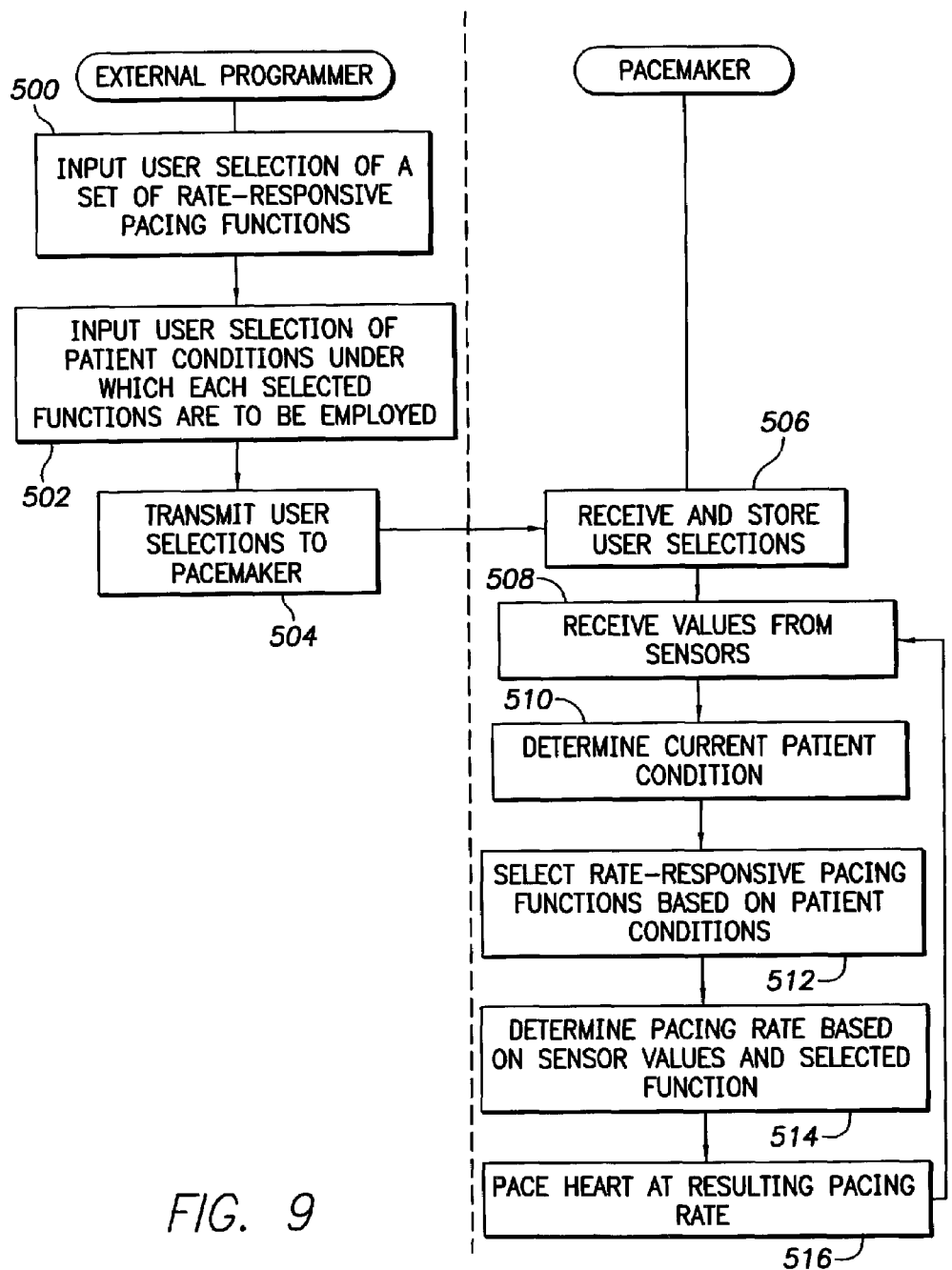
FIG. 9 is a flow chart illustrating an exemplary method for programming the implanted device of FIGS. 2 and 3 using the external programmer of FIG. 4 wherein the implanted device is programmed with a plurality of rate-response functions for use under different patient conditions.

The flow chart of FIG. 9 illustrates the programming of multiple rate-responsive pacing functions for use under different patient conditions within a cardiac stimulation device implanted within a patient. At step 500, rate-responsive pacing programming unit 203 of the external programmer (FIG. 4) displays a list of the sensors within the implanted device and the physician selects one of the sensors. At step 502, the programmer displays a list of pre-determined patient conditions or states, such as a textual list identifying: "bed rest"; "active"; "frequent vasovagal syncope"; "frequent tachyarrhythmia"; "frequent premature atrial contractions (PACs)"; "frequent premature ventricular contractions (PVCs)"; and the like. The physician selects a set of patient conditions and, for each selected condition, the programmer displays a default rate-responsive pacing function. Exemplary default functions for use with a minute ventilation sensor for an active state 503 and a bed rest state 505 are shown in FIG. 10. Using the techniques of FIG. 5, the physician may adjust the default functions as desired.

The selected patient conditions and the corresponding sensor response functions are transmitted to the implanted device for storage therein at steps 504 and 506. Beginning at step 508, the rate-responsive pacing controller of the implanted device (unit 61 of FIG. 4) receives values from various sensors of the device and at step 510 determines the current condition or state of the patient. At step 512, the device selects a sensor response function based on the detected condition of the patient, then at step 514 determines the pacing rate using the selected response function. At step 516, the device paces the heart at the resulting pacing rate. In this manner, the pacing rate is derived from a sensor response function tailored to the current condition of the patient. Hence, for example, a more aggressive rate-responsive pacing function may be used while the patient is generally active than while the patient is in prolonged bed rest. A more aggressive rate-responsive pacing function also may be used if the patient has frequent tachyarrhythmia episodes following mode-switching events. A less aggressive rate-responsive pacing function may be employed if the patient has frequent PACs or PVCs. Note that the sensors used to determine the condition of the patient are typically not the same sensors as specified in steps 500 to 504. The device may, for example, determine whether the patient is generally active or in a state of prolonged bed rest based on values received from an activity variance sensor, then use minute ventilation sensor values to derive the pacing rate. Bed rest may also be detected based on prolonged shallow breathing as determined, for example, by a blood oxygen saturation sensor.

What have been described are various techniques for 1) generating smooth user-selected rate-responsive pacing functions, 2) programming user-selected percentage contribution functions for different sensors, and 3) programming separate rate-responsive pacing functions for use under different patient conditions. The various techniques may be combined. For example, an external programmer may be provided which permits a physician to generate multiple smooth rate response functions for each sensor for use under different conditions and to further specify the percent contributions of the sensors to determining a final pacing rate. The techniques of the invention may also be employed in connection with programming dynamic atrial overdrive pacing techniques for devices capable of performing overdrive pacing. For example, the aforementioned techniques for generating smooth rate-responsive pacing functions may be employed to generate smooth overdrive pacing functions as well. Details regarding overdrive pacing techniques may be found in U.S. Pat. No. 6,058,328 to Levine et al. and in U.S. patent application Ser. No., 10/043,781, filed January, 2002, entitled "Method and Apparatus for Dynamically Adjusting a Non-linear Overdrive Pacing Response Function", of Florio at al., which are both incorporated by reference herein.

The various functional components of the exemplary system may be implemented using any appropriate technology including, for example, microprocessors running software programs or application specific integrated circuits (ASICs) executing hard-wired logic operations. Although described with respect to a pacemakers and ICDs used in conjunction with an external programmer, aspects of the invention are applicable to other systems, such as systems employing other implantable cardiac stimulation devices or systems employing other types of external interfaces for use with the implantable device. The exemplary embodiments of the invention described herein are merely illustrative of the invention and should not be construed as limiting the scope of the invention.

What is claimed is:

1. In an external programmer for use in programming an implantable cardiac stimulation device having at least one sensor for use in rate-responsive pacing, a programming method comprising:

inputting a set of individual values representative of points defining a desired rate-responsive pacing function;

fitting a curvilinear function to the input values to generate a rate-responsive pacing function from the input values; and transmitting the rate-responsive pacing function to the implantable cardiac stimulation device for use therein in determining a rate-responsive pacing rate.

2. The method of claim 1 for use in programming a cardiac stimulation device having a plurality of sensors and wherein the method further comprises inputting a value identifying the particular sensor for which the rate-responsive pacing function is to be generated.

3. The method of claim 2 for use in programming a cardiac stimulation device having a plurality of sensors wherein the pacing rate is calculated based on a combination of values from the sensors and wherein the method further comprises:

inputting contribution values representative of relative contributions each sensor of the implantable cardiac stimulation device is to provide in deriving a rate-responsive pacing rate; and transmitting the contribution values to the cardiac stimulation device for use therein.

4. The method of claim 3 for use in programming a cardiac stimulation device capable of detecting an activity level of the patient and wherein the method further comprises:

inputting separate sets of contribution values to be used by the cardiac stimulation device for separate activity levels; and transmitting the separate sets of contribution values to the cardiac stimulation device for use therein along with the associated activity levels.

5. The method of claim 1 for use in programming a cardiac stimulation device having one or more of an orthostatic sensor, an activity sensor, a minute ventilation sensor, a vasovagal syncope sensor, a paced depolarization integral sensor, a QT interval sensor, a temperature sensor, an oxygen blood saturation sensor, and a pre-ejection period sensor and wherein inputting a set of individual values representative of points defining a desired rate-responsive pacing function is performed to input pacing rates for various values expected from the particular sensor.

6. The method of claim 1 wherein, for a particular sensor, inputting a set of individual values, fitting a curvilinear function to the input values to generate a rate-responsive pacing function, and transmitting the rate-responsive pacing function to the cardiac stimulation device are performed a plurality of times to program the device with a plurality of rate-responsive pacing functions for the particular sensor.

7. The method of claim 6 wherein the method further comprises:

inputting criteria specifying circumstances under which each of the plurality of rate-responsive pacing functions is to be employed by the cardiac stimulation device; and transmitting the criteria to the cardiac stimulation device for use therein such that the cardiac stimulation device may be programmed to use different rate-responsive pacing functions under different conditions.

8. The method of claim 7 for use in programming a cardiac stimulation device capable of detecting when the patient is in a bed-rest state and wherein the criteria input specifies that a selected rate-responsive pacing function is to be employed while the bed-rest state is detected.

9. The method of claim 7 for use in programming a cardiac stimulation device capable of detecting when the patient is in an active state and wherein the criteria input specifies that a selected rate-responsive pacing function is to be employed while the active state is detected.

10. The method of claim 7 for use in programming a cardiac stimulation device capable of mode switching and capable of detecting tachyarrhythmia episodes and wherein the criteria input specifies that a selected rate-responsive pacing function is to be employed whenever a predetermined number of tachyarrhythmia episodes are detected following mode switching episodes within a predetermined time period.

11. The method of claim 7 for use in programming a cardiac stimulation device capable of detecting premature atrial contractions and wherein the criteria input specifies that a selected rate-responsive pacing function is to be employed whenever a predetermined number of premature atrial contractions are detected within a predetermined time period.

12. The method of claim 7 for use in programming a cardiac stimulation device capable of detecting premature ventricular contractions and wherein the criteria input specifies that a selected rate-responsive pacing function is to be employed whenever a predetermined number of premature ventricular contractions are detected within a predetermined time period.

13. The method of claim 1 further comprising converting the rate-responsive pacing function to a look-up table of pacing rates as a function of sensor values and wherein transmitting the rate-responsive pacing function to the cardiac stimulation device is performed by transmitting the look-up table to the cardiac stimulation device.

14. A method of programming a cardiac stimulation device having at least one sensor for use in rate-responsive pacing, the method comprising:

inputting a set of individual values representative of points defining a desired rate-responsive pacing function using an external programmer, fitting a curvilinear function to the input values to generate a rate-responsive pacing function, and transmitting the rate-responsive pacing function to the cardiac stimulation device; and receiving the rate-responsive pacing function within the cardiac stimulation device and converting sensor output values to pacing rates using the rate responsive pacing function.

15. In an external programmer for use in programming an implantable cardiac stimulation device having at least one sensor for use in rate-responsive pacing, a system comprising:

a rate-responsive pacing programming unit operative to input a set of individual values representative of points defining a desired rate-responsive pacing function and to fit a curvilinear function to the input values to generate a rate-responsive pacing function; and a telemetry unit adapted to transmit the rate-responsive pacing function to the cardiac stimulation device for use therein in determining a rate-responsive pacing rate.

16. A system comprising:

an external programmer having a rate-responsive pacing programming unit operative to input a set of individual values representative of points defining a desired rate-responsive pacing function and to fit a curvilinear function to the input values to generate a rate-responsive pacing function, and a telemetry unit operative to transmit the rate-responsive pacing function to the cardiac stimulation device; and an implantable cardiac stimulation device having a rate-responsive sensor, a telemetry unit operative to receive the rate-responsive pacing function from the external programmer, and a rate-responsive pacing controller operative to convert output values from the rate-responsive sensor to pacing rates using the rate-responsive pacing function.

17. In an external programmer for use in programming an implantable cardiac stimulation device having at least one sensor for use in rate-responsive pacing, a method comprising:

inputting a set of individual values representative of points defining a desired rate-responsive pacing function;

fitting a curvilinear function to the input values to generate a rate responsive pacing function;

converting the rate-responsive pacing function to a look-up table of pacing rates as a function of sensor values; and transmitting the look-up table to the cardiac stimulation device for use therein in determining a rate-responsive pacing rate.

18. A system comprising:

an implantable cardiac stimulation device;

an external programmer to program the implantable cardiac stimulation device;

means, within the external programmer, for inputting a set of individual values representative of points defining a desired rate-responsive pacing function;

means, within the external programmer, for fitting a curvilinear function to the input values to generate a rate-responsive pacing function;

means, within the external programmer, for converting the rate-responsive pacing function to a look-up table of pacing rates as a function of sensor values;

means, within the external programmer, for transmitting the look-up table to the implantable cardiac stimulation device for use therein in determining a rate-responsive pacing rate;

means, within the implantable cardiac stimulation device, for receiving the look-up table; and means, within the implantable cardiac stimulation device, for converting sensor output values to pacing rates using the look-up table.

* * * * *